(12) United States Patent
Saidian et al.

(10) Patent No.: US 10,578,568 B2
(45) Date of Patent: Mar. 3, 2020

(54) WATER/OIL/GAS EMULSIONS/FOAMS CHARACTERIZATION USING LOW FIELD NUCLEAR MAGNETIC RESONANCE

(71) Applicant: Colorado School of Mines, Golden, CO (US)

(72) Inventors: Milad Saidian, Houston, TX (US); Ahmad A. Abdul Majid, Golden, CO (US); Manika Prasad, Golden, CO (US); Carolyn A. Koh, Lafayette, CO (US)

(73) Assignee: Colorado School of Mines, Golden, CO (US)

( * ) Notice: Subject to any disclaimer, the term of this patent is extended or adjusted under 35 U.S.C. 154(b) by 729 days.

(21) Appl. No.: 15/143,000

(22) Filed: Apr. 29, 2016

(65) Prior Publication Data

US 2016/0320323 A1 Nov. 3, 2016

Related U.S. Application Data

(60) Provisional application No. 62/154,638, filed on Apr. 29, 2015.

(51) Int. Cl.
| | |
|---|---|
| *E21B 47/06* | (2012.01) |
| *E21B 49/08* | (2006.01) |
| *G01N 24/08* | (2006.01) |
| *G01R 33/44* | (2006.01) |

(52) U.S. Cl.
CPC ......... *G01N 24/081* (2013.01); *G01R 33/445* (2013.01)

(58) Field of Classification Search
CPC .... G01N 24/081; G01N 24/08; G01N 24/082; E21B 2049/085; E21B 47/06; E21B 49/08
See application file for complete search history.

(56) References Cited

U.S. PATENT DOCUMENTS

| | | | |
|---|---|---|---|
| 3,419,795 A | 12/1968 | Genthe et al. | |
| 4,785,245 A | 11/1988 | Lew et al. | |
| 2003/0009297 A1 | 1/2003 | Mirotchnik et al. | |
| 2008/0221800 A1 | 9/2008 | Gladkikh et al. | |
| 2009/0256562 A1* | 10/2009 | Gao ..................... | G01N 24/08 324/308 |

(Continued)

OTHER PUBLICATIONS

Aichele et al., "Water in oil emulsion droplet size characterization using a pulsed field gradient with diffusion editing (PFG-DE) NMR technique," Journal of Colloid and Interface Science, 2007, vol. 315(2), pp. 607-619.

(Continued)

*Primary Examiner* — Zakiya W Bates
(74) *Attorney, Agent, or Firm* — Sheridan Ross P.C.

(57) ABSTRACT

Methods to identify and quantify the emulsion properties in oil and gas producing wells at downhole condition or pipelines using NMR and to provide potential treatment options. The longitudinal ($T_1$), transverse ($T_2$) relaxation times and diffusion coefficient of a fluid are changed by the presence of a second dispersed fluid phase in the form of bubbles or droplets. Properties may be determined by comparing the measured $T_1$ and $T_2$ spectra and diffusion coefficient at downhole conditions with the bulk responses of the constituent fluids.

12 Claims, 11 Drawing Sheets

(56) References Cited

U.S. PATENT DOCUMENTS

| | | | |
|---|---|---|---|
| 2012/0209541 A1* | 8/2012 | Ong | G01F 1/74 |
| | | | 702/45 |
| 2014/0002081 A1 | 1/2014 | Mitchell et al. | |
| 2014/0026786 A1* | 1/2014 | Jaffel | B28C 5/383 |
| | | | 106/680 |
| 2016/0320323 A1 | 11/2016 | Saidian | |

OTHER PUBLICATIONS

Barrett et al., "MRI of Tumor Angiogenesis," Journal of Magnetic Resonance Imaging, 2007, vol. 26, pp. 235-249.

Coates et al., NMR Logging Principles and Applications: Haliburton Energy Services Publication, 1999, 251 pages, uploaded in 3 parts.

Delgado-Linares et al., "Model Water-in-Oil Emulsions for Gas Hydrate Studies in Oil Continuous Systems," Energy Fuels, 2013, vol. 27(8), pp. 4564-4573, 10 pages.

Dunn et al., "Nuclear Magnetic Resonance Petrophysical and Logging Applications," 1st edition, Pergamon, 2002, vol. 32, abstract only, 3 pages.

Fridjonsson et al., "Determination of mean droplet sizes of water-in-oil emulsions using an Earth's field NMR instruction," Journal of Magnetic Resonance, 2012, vol. 221, pp. 97-102.

Hurlimann et al., "Diffusion-Editing: New NMR Measurement of Saturation and Pore Geometry," Society of Petrophysicists and Well-Log Analysts, 2002, SPWLA 43rd Annual Logging Symposium, Oiso, Japan, abstract only, 2 pages.

Johns, "NMR studies of emulsions," Current Opinion in Colloid & Interface Science, 2009, vol. 14(3), pp. 178-183, abstract only, 2 pages.

Murday et al., "Self-Diffusion Coefficient of Liquid Lithium," The Journal of Chemical Physics, 1968, vol. 48, pp. 4938-4944, abstract only, 1 page.

Noik et al., "Design of a Crude Oil Dehydration Unit," Society of Petroleum Engineers, 2002, SPE-77492-MS, abstract only, 2 pages.

Opedal et al., "Methods for Droplet Size Distribution Determination of Water-in-oil Emulsions Using Low-Field NMR," Journal for the Basic Principles of Diffusion Theory, Experiment and Application, 2009, vol. 9, pp. 1-29.

Packer et al., "Pulsed NMR Studies of Restricted Diffusion: I. Droplet size distribution," Journal of Colloid and Interface Science, 1971, vol. 40(2), pp. 206-218, abstract only, 2 pages.

Pena et al., "Enhanced characterization of oilfield emulsions via NMR diffusion and transverse relaxation experiments," Advances in Colloid and Interface Science, 2003, vol. 105, pp. 103-150.

Peixinho et al., "Rheology of Hydrate Forming Emulsions," American Chemical Society, 2010, vol. 26(14), pp. 11699-11704.

Sjoblom et al., "Investigation of the Hydrate Plugging and Non-Plugging Properties of Oils," Journal of Dispersion Science and Technology, 2010, vol. 31(8), pp. 1100-1119, abstract only, 2 pages.

Sloan et al., "Clathrate Hydrates of Natural Gases," Third Edition, CRC Press, 2007, abstract only, 2 pages.

Song, "Recent progress of nuclear magnetic resonance applications in sandstones and carbonates rocks," Vadose Zone Journal, 2010, vol. 9, pp. 828-834.

Sorland et al., "Rapid characterization of emulsions by pulsed field gradient nuclear magnetic resonance," Journal for the Basic Principles of Diffusion Theory, Experiment and Application, 2013, vol. 19, pp. 1-16.

Turner et al., "Methane hydrate formation and an inward growing shell model in water-in-oil dispersions," Chemical Engineering Science, 2009, vol. 64(18), pp. 3996-4004.

Venkataramanan et al., "Solving Fredholm integrals of the first kind with tensor product structure in 2 and 2.5 dimensions," IEEE Transactions on Signal Processing, 2002, vol. 50(5), 1017-1026, abstract only, 4 pages.

Turner, "Clathrate Hydrate Formation in Water-In-Oil Dispersions," Colorado School of Mines, 2005, 213 pages.

Alcantar-Lopez et al., "Improving Our Understanding of Porosity in Source Rock Reservoirs through Advanced Imaging Techniques," Unconventional Resources Technology Conference, URTeC 1619700, Aug. 2013, abstract only.

Aliyev, "Rock Typing in Tight Gas Sands: A Case Study in Lance and Mesaverde Formations from Jonah Field," M.S. Thesis, Colorado School of Mines, 2015, retrieved from https://dspace.library.colostate.edu/bitstream/handle/11124120145/Aliyev_mines_0052N_10780.pdf?sequence=1, 83 pages.

Allen et al., "How to Use Borehole Nuclear Magnetic Resonance," Oilfield Review, 1997, pp. 34-57.

Ambrose et al., "New Pore-scale Considerations for Shale Gas in Place Calculations," Society of Petroleum Engineers Unconventional Gas Conference, SPE-131772, 2010, 17 pages.

Andra et al., "Digital rock physics benchmarks—Part I: Imaging and segmentation," Computers and Geosciences, vol. 5, 2013, pp. 25-32.

Balinov et al., "The NMR Self-Diffusion Method Applied to Restricted Diffusion. Simulation of Echo Attenuation from Molecules in Spheres and between Planes," Journal of Magnetic Resonance Series A, vol. 104, No. 1, Aug. 1993, pp. 17-25.

Barrett et al., "The Determination of Pore Volume and Area Distributions in Porous Substances: I. Computations From Nitrogen Isotherms," Journal of the American Chemicy Society, vol. 73, No. 1, Jan. 1951, pp. 373-380.

Brown et al., "Southern Piceance Basin Model—Cozzette, Corcoran and Rollins Sandstones," American Association of Petroleum Geologists Studies in Geology, vol. 24, 1986, pp. 207-219, abstract only.

Buess et al., "Acoustic ringing effects in pulsed nuclear magnetic resonance probes," Review of Scientific Instruments, vol. 49, No. 8, 1978, pp. 1151-1155, abstract only.

Butler et al., "Estimating Solutions of First Kind Integral Equations with Nonnegative Constraints and Optimal Smoothing," SIAM Journal of Numerical Analysis, vol. 18, No. 3, 1981, pp. 381-397, abstract only.

Carr et al., "Effects of Diffusion on Free Precession in Nuclear Magnetic Resonance Experiments," Physical Review, vol. 94, No. 3, May 1954, pp. 630-638, abstract only.

Chan et al., "Characterization and correction of eddy-current artifacts in unipolar and bipolar diffusion sequences using magnetic field monitoring," Journal of Magnetic Resonance, vol. 224, Jul. 2014, pp. 74-84.

Chi et al., "Quantifying the Impact of Natural Fractures and Pore Structure on NMR Measurements in Multiple-Porosity Systems," International Petroleum Technology Conference, Jan. 2014, 12 pages, abstract only.

Dunn et al., "On the Calculation of NMR Relaxation Time Distributions," Society of Petroleum Engineers Annual Technical Conference and Exhibition, SPE-28367, 1994, 10 pages, abstract only.

Freedman et al., "Wettability, Saturation, and Viscosity Using the Magnetic Resonance Fluid Characterization Method and New Diffusion-Editing Pulse Sequences," Society of Petroleum Engineers Annual Technical Conference and Exhibition, SPE-77397-MS, Sep. 2002, 13 pages, abstract only.

Harkins et al., "Surfaces of Solids. XII. An Absolute Method for the Determination of the Area of a Finely Divided Crystalline Solid," Journal of the American Chemical Society, vol. 66, No. 8, 1944, pp. 1362-1366, abstract only.

Howard, "Porosimetry Measurement of Shale Fabric and its Relationship to Illite/Smectite Diagenesis," Clays and Clay Minerals, vol. 39, No. 4, 1991, pp. 355-361.

Hurlimann et al., "Quantitative Measurement of Two-Dimensional Distribution Functions of Diffusion and Relaxation in Grossly Inhomogeneous Fields," Journal of Magnetic Resonance, vol. 157, No. 1, Jul. 2002, pp. 31-42, abstract only.

Hurlimann, "Effective Gradients in Porous Media Due to Susceptibility Differences," Journal of Magnetic Resonance, vol. 131, No. 2, Apr. 1998, pp. 232-240, abstract only.

Jiang et al., "Integrated Petrophysical Interpretation of Eagle Ford Shale with 1-D and 2-D Nuclear Magnetic Resonance (NMR)," Society of Petrophysicists and Well Log Analysts Annual Logging Symposium, No. 54, Jun. 2013, 22 pages, abstract only.

(56) References Cited

OTHER PUBLICATIONS

Kenyon, "Nuclear magnetic resonance as a petrophysical measurement," Nuclear Geophysics, vol. 6, No. 2, 1992, pp. 153-171, abstract only.
Kenyon, "Petrophysical Principles of Applications of NMR Logging," The Log Analyst vol. 38, No. 2, Mar. 1997, 23 pages, abstract only.
Kleinberg, "NMR Well Logging at Schlumberger," Concepts in Magnetic Resonance, vol. 13, No. 6, 2001, pp. 396-403.
Kulia et al., "Compositional Controls on Mudrock Pore-Size Distribution: An Example from Niobrara Formation," SPE Annual Technical Conference and Exhibition, Oct. 2012, abstract only.
Kulia et al., "Measurement and interpretation of porosity and pore-size distribution in mudrocks: The hole story of shales," Ph.D. Thesis, Colorado School of Mines, 2013, 269 pages.
Kulia et al., "Specific surface area and pore-size distribution in clays and shales," Geophysical Prospecting, vol. 61, 2013. pp. 341-362.
Latorraca et al., "Heavy Oil Viscosity Determination Using NMR Logs," SPWLA 40th Annual Logging Symposium, May 1999, abstract only.
Latour et al., "Pore-Size Distributions and Tortuosity in Heterogeneous Porous Media," Journal of Magnetic Resonance A, vol. 112, No. 1, Jan. 1995, pp. 83-91, abstract only.
Lewis et al., "NMR T2 Distributions in the Eagle Ford Shale: Reflections on Pore Size," SPE Unconventional Resources Technology Conference Paper No. 164554, 2013, 15 pages, abstract only.
Machado et al., "Carbonate Petrophysics in Wells Drilled with Oil-Base Mud," SPWLA 52nd Annual Logging Symposium, May 2011, 10 pages.
Marschall et al., "Method for Correlating NMR Relaxometry and Mercury Injection Data," SCA Conference Paper No. 9511, 1995, 12 pages.
Meiboom et al., "Modified SpinEcho Method for Measuring Nuclear Relaxation Times," AIP Review of Scientific Instruments, vol. 29, No. 8. Aug. 1958, pp. 688-691.
Mitra et al., "Effects of microgeometry and surface relaxation on NMR pulsed-field-gradient experiments: Simple pore geometries," Physics Review B., vol. 45, No. 1, Jan. 1992, pp. 143-156, abstract only.
Pape et al., "Pore geometry of sandstone derived from pulsed field gradient NMR," Journal of Applied Geophysics, vol. 58, No. 3, Mar. 2006, pp. 232-252, abstract only.
Passey et al., "From Oil-Prone Source Rock to Gas-Producing Shale Reservoir—Geologic and Petrophysical Characterization of Unconventional Shale-Gas Reservoirs," Society of Petroleum Engineers, SPE Paper No. 131-350, Jun. 2010, 29 pages.
Price, "Pulsed-Field Gradient Nuclear Magnetic Resonance as a Tool for Studying Translational Diffusion: Part 1. Basic Theory," Concepts in Magnetic Resonance, vol. 9, No. 5, 1997, pp. 299-336.
Rivera et al., "Effect of Mineralogy on NMR, Sonic, and Resistivity: A Case Study of the Monterey Formation," SPE Unconventional Resources Technology Conference Paper No. 1922872, 2014, 20 pages.
Stejskal et al., "Spin Diffusion Measurements: Spin Echoes in the Presence of a Time-Dependent Field Gradient," Journal of Chemical Physics, vol. 42, No. 1, Jan. 1965, pp. 288-292.
Straley et al., "Core Analysis by Low Field NMR," Log Analyst, vol. 38, No. 2, 1994, p. 43-56.
Sun et al., "Two-dimensional nuclear magnetic resonance petrophysics," Magnetic Resonance Imaging, vol. 23, No. 2, Feb. 2005, pp. 259-262, abstract only.
Talabai, "Pore-Scale Simulation of NMR Response in Porous Media," Ph.D. Thesis, Imperial College, Sep. 2008, 163 pages.
Tanner, "Use of Stimulated Echo in NMR Diffusion Studies," Journal of Chemical Physics, vol. 52, No. 5, 1970, pp. 2523-2526, abstract only.
Timur, "Pulsed Nuclear Magnetic Resonance Studies of Porosity, Movable Fluid, and Permeability of Sandstones," Journal of Petroleum Technology, vol. 21, No. 6, Jun. 1969, 12 pages, abstract only.
Toumelin et al., "Limits of 2D NMR Interpretation Techniques to Quantify Pore Size, Wettability, and Fluid Type: A Numerical Sensitivity Study," SPE Journal, vol. 11, No. 3, Sep. 2006, pp. 354-363.
Whittal et al., "Quantitative interpretation of NMR relaxation data," Journal of Magnetic Resonance, vol. 84, No. 1, Aug. 1989, pp. 134-152, abstract only.
Official Action for U.S. Appl. No. 14/941,310, dated Oct. 18, 2018, 10 pages.

\* cited by examiner

WATER/OIL/GAS EMULSIONS/FOAMS CHARACTERIZATION USING LOW FIELD NUCLEAR MAGNETIC RESONANCE

CROSS REFERENCE TO RELATED APPLICATIONS

This application claims priority and the benefit under 35 U.S.C. § 119(e) to U.S. Provisional Patent Application Ser. No. 62/154,638 filed Apr. 29, 2015, which is incorporated herein in its entirety by reference.

FIELD OF THE INVENTION

This invention relates to a method for measuring the bubble/droplet size distribution at oil and gas producing wells and pipelines for flow assurance, fluid property analysis and production evaluation in oil and gas producing wells. The method can be used to assess gas hydrate slurry formation and hydrate plugging risk to mitigate the formation and risk.

BACKGROUND

Problems can occur when oil and gas are both present in the produced fluids. The gas can be present (and usually is) in a dissolved phase. During production, the pressure decreases. If pressure goes below the bubble point, gas will come out of solution causing flow reduction and possibly blockage of production. Further, if gas comes out of solution, hydrates might form, again leading to blockage or reduction of production. Turbulent flow in the oil and gas pipelines often results in the formation of a water-in-oil (W/O) emulsion. Small water droplets in the pipeline provide large total surface area for hydrate formation at the water/gas saturated oil interface, which can lead to full conversion of water to gas hydrate. Hydrate formation can begin with water being emulsified in the oil phase forming water-in-oil (W/O) emulsions. The water molecules form a network of hydrogen bonds around the gas molecules creating water cages. Gas hydrates, (also known as clathrate hydrates) are crystalline compounds in which small gas molecules such as methane, ethane, propane are enclathrated by hydrogen-bonded water molecules. Gas hydrates typically form at high pressure and low temperature (e.g. 10 MPa, 277 K for methane hydrates). At these conditions, hydrates can form and potentially plug subsea oil and gas pipelines. Since these hydrates disrupt flow, they are considered a nuisance and can cause considerably expense due to disruption of production. It is thus of particular interest to determine the water droplet size of an emulsion and to use this information to effectively prevent the formation of these hydrates. Since water droplet size of the emulsion provides information about the hydrate particle size in the slurry, it is crucial to determine the water droplet size in a W/O emulsion.

Other measurements are also important to determining the impact of hydrate slurry or plug formation. Emulsion properties can impact hydrate slurry/plug formation, i.e. whether the system is fully dispersed with all water emulsified in oil, or partially dispersed where water is emulsified in oil and a free water phase also exists, or water continuous. Thus, it is also crucial to determine water droplet size distributions (DSD) in an emulsion. Measurement of PVT properties of oil such as bubble point pressure, viscosity and water cut is crucial in reservoir performance evaluation. Downhole viscosity measurements require a special production logging tool which are time consuming and expensive. In many occasions, lack of proper sealing of the tool or sampling a non-productive portion of the wellbore results in a significant cost and waste of variable time. Also current production logging technologies measure the oil/water/gas ratios by sampling a very limited portion of the fluid using point wise sensors which suffer from inaccuracy due to the improper sampling of the fluid.

FIG. 1 (redrawn from Turner, D. J. *Colorado School of Mines*, 2006 and Turner, D. J et al., *Chem. Eng. Sci.* 2009, 64 (18), 3996. doi: 1110.1016/j.ces.2009.05.051) illustrates a conceptual schematic of hydrate formation in pipelines for an oil-dominated system (i.e. where oil is the continuous phase). Hydrate formation begins with water being emulsified in the oil phase forming a water-in-oil (W/O) emulsion. This emulsion may or may not be desirable depending on the size of the water droplets. Next, at appropriate pressure and temperature condition, a thin hydrate shell will grow around the water droplets. If the water droplet is in the µm size range, gas molecules are able to penetrate through the shell. In this case, hydrates will grow inward forming fully converted hydrate particles that can prevent hydrate agglomeration and pipeline blockage. However, this hydrate shells can create a gas diffusion barrier between the oil and the water phase if water droplets are bigger than µm size range. Then there will be capillary attraction forces between hydrate particles due to water bridging (from unconverted free water) that cause the particles to agglomerate forming large hydrate aggregates. Since these aggregates may then form a blockage in the pipeline, it is crucial to determine the water droplet size in an emulsion and eventually the hydrate particle size in a slurry. With this information, pipeline parameters can be changed and the necessary channels injected to prevent the formation of large hydrate aggregates.

There are several methods being employed by researchers and operators to determine droplet size of the emulsion such as microscopy, and Nuclear Magnetic Resonance (NMR). Each method has its own advantages and disadvantages. For instance, the microscopy imaging method is relatively simple and fast. The size of the droplet is measured by analyzing optical microscopy images of the emulsion. However, in this method, only a small sample of the emulsion is analyzed (e.g. ~250 water droplets) and thus the method may not reflect the actual condition in pipelines. Another method to determine the DSD of emulsions is using NMR. This method has gained interest since it is non-destructive and can measure a considerable amount of sample.

Low field nuclear magnetic resonance (NMR) measurements are currently used to measure porosity, pore size distribution and fluid saturations in oil and gas producing wells at downhole conditions. Hydrogen relaxation in different fluids is the key to identify fluid type and saturation in the formation. Besides relaxation, NMR downhole tools are capable of measuring the fluid diffusion in oil, gas and water and differentiating between these fluids based on diffusion coefficient differences. Both the relaxation rate and the diffusion coefficient of fluids change when restricted in non-permeable boundaries such as rock grains, bubbles or droplets.

Thus, there is a need for a system and method that can be used to predict whether a hydraulic plug is forming in an emulsion or foam, and utilize this information to design an appropriate treatment protocol.

SUMMARY

The present invention provides a direct and reliable technique to characterize the production stream and is the only tool that provides information about the emulsion type and droplet/bubble size. The present invention takes advantage of a correlation between the change in size of restricted fluid and change in relaxation rate and diffusion coefficient. Thus, with proper calibrations the NMR tool can be used to characterize emulsions. This information can then be used to prevent hydrate formation by determining necessary hydrate management strategies and treatments. The information can also provide a variable for simulation to better determine the amount of hydrate that will form in the production stream.

Low-field NMR is a tool used in reservoir characterizations. The "normal" uses of this tool have been previously discussed. While the tool can still be used for these analyses, the present invention allows for NMR to be used for wider applications, including during oil/gas production rather than before production when the technology is used to determine how much production can be expected.

The present invention relates to methods and systems to identify and quantify the emulsion properties in oil and gas producing wells at downhole condition or pipelines using NMR. The Diffusion-Transverse Relaxation ($T_2$) or Diffusion-Longitudinal Relaxation ($T_1$) times and diffusion coefficient of a fluid are changed by the presence of a second dispersed fluid phase in the form of bubbles or droplets. The NMR system is calibrated with the bulk relaxation of the produced fluids at surface conditions. Comparing the measured $T_1$ and $T_2$ spectra and diffusion coefficient at downhole conditions with the bulk responses of the constituent fluids determines the dispersed and continuous phases, droplet/bubble size distribution and Pressure-Volume-Temperature (PVT) properties of the produced oil such as bubble point pressure and viscosity. The production stream in oil and gas producing wells usually is in the form of an oil/water/gas emulsion. Characterizing the emulsion type (dispersed vs. continuous phase), droplet/bubble size, point of gas expulsion from oil, and identifying the problematic perforations are of importance for production and equipment planning, and reservoir and fluid characterization.

The present invention can also be utilized as a production logging tool. It can be used by various service companies providing logging services to oil and gas producing companies. The acquired data can be used to resolve the aforementioned changes and optimize well production.

The present invention relates to a method for bubble/droplet size distribution measurement at oil and gas producing wells and pipelines for flow assurance, fluid property analysis and production evaluation in oil and gas producing wells. In this invention, multiple $T_2$ or $T_1$ measurements are required to calculate the average surface relaxivity. Using the calculated average surface relaxivity fast $T_1$ and $T_2$ measurements along the pipeline and well bore can be converted to droplet or bubble size.

The main applications of this invention are:

(a) Characterization of the fluid flowing inside on-shore and subsea pipeline. Using this technique the bubble/droplet size profile of the pipeline at any point can be determined. These profiles lead to better understanding of the possibility of hydrate formation, and the prevention thereof;

(b) Characterization of the production fluid at downhole conditions for oil and gas producing wells. Oil, water and gas usually flow simultaneously in the wellbore. Locating the depth that gas is expelled from the oil due to pressure drop determines the bubble point pressure of the oil. Variation in $T_2$ distribution of the oil as a result of gas expulsion is an indication of the viscosity change;

(c) Perforations are used to connect the oil and gas producing formations to the wellbore. The efficiency of the perforation is critical for production evaluation of each well. This invention can be used to evaluate the oil, water and gas production from each perforation by performing the measurements at perforation depth;

(d) In medical MRI, contrast agents are used to assess tumors and vessel permeability (Barrett et al., 2007). For example, onset of arteriosclerosis can be estimated more precisely by combining this technique with traditional MRI scans. This NMR technique can also improve microbubble-enhanced ultrasonic testing to measure blood vessel perfusion and blood volume.

An aspect of the invention is a method of assessing gas hydrate slurry formation and a hydrate plugging risk by determining the droplet size distribution of an oil-in-water or an water-in-oil emulsions. The method includes providing a low field NMR relaxometer to a emulsion, wherein the low field NMR relaxometer is capable of measuring transverse relaxation ($T_2$), and 2D diffusion coefficient-transverse relaxation (D-$T_2$). The $T_2$ and the D-$T_2$ for bulk fluids present in the slurry are measured. A characteristic of the $T_2$ and the D-$T_2$ is defined for each individual fluid constituent of the slurry. $T_2$ and the D-$T_2$ are measured for at least three samples of the slurry. Oil peaks and water peaks are identified for the three samples. The diffusion coefficient of a discontinuous phase of the slurry is converted to droplet size using a restricted diffusion model in droplets for the samples. The surface relaxivity of the slurry is calculated by combining a radius of the droplet and the $T_2$ for the three samples. A $T_2$ distribution is measured for the three samples, and the $T_2$ distribution are converted to droplet size distribution with the surface relaxivity. Finally, the droplet size distribution information is compared with a database of droplet size distribution date to assess the relative risk of hydrate formation.

An aspect of the invention is a method to determine a bubble size distribution in an oil and gas foam. The method includes providing a low field NMR relaxometer, wherein the low field NMR relaxometer is capable of measuring at least one of a transverse relaxation ($T_2$), and a 2D diffusion coefficient-transverse relaxation (D-$T_2$). The $T_2$ and D-$T_2$ are measured for the produced fluids in the emulsion. Oil peaks and water peaks are identified from a CPMG pulse sequence for the emulsion. The bubble size distribution can be determined from the foam.

An aspect of the invention is a method to determine a droplet size distribution of an emulsion. The emulsion is one of an oil-in-water emulsion or a water-in-oil emulsion. The method includes providing a low field NMR relaxometer wherein the low field NMR relaxometer is capable of measuring at least one of a transverse relaxation ($T_2$), and a 2D diffusion coefficient-transverse relaxation (D-$T_2$). The $T_2$ and D-$T_2$ are measured for produced fluids in the emulsion. Oil peaks and water peaks are identified from a CPMG pulse sequence for the emulsion. The D-$T_2$ of the discontinuous phase is converted to bubble size using a restricted diffusion model in bubbles. The surface relaxivity of a foam is calculated by combining a droplet radius and longitudinal relaxation ($T_1$) for the produced fluids in the emulsion. The $T_1$ is measured for the emulsion. The droplet size distribution can be determined in the emulsion.

These and other advantages will be apparent to one skilled in the art in view of this disclosure.

DETAILED DESCRIPTION

Figure 1:
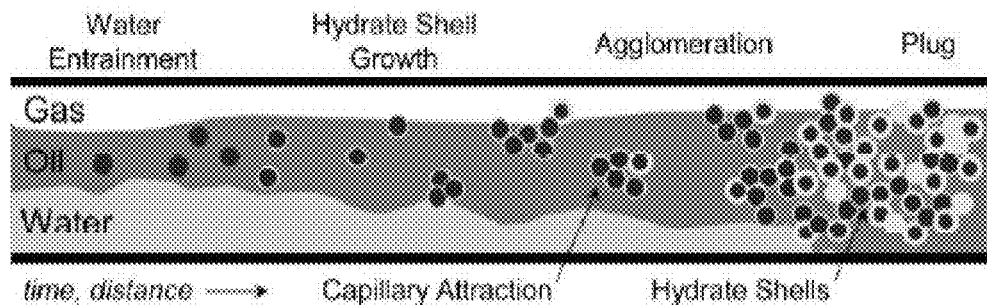
FIG. 1 illustrates a conceptual schematic of hydrate formation in pipelines for an oil-dominated system (i.e. where oil is the continuous phase)

The present invention includes a method to characterize water, gas and oil emulsions and mixtures. Using this method the size of bubble or droplets can be determined. The bubble point pressure can be estimated at downhole conditions in oil and gas producing wells. The following terms are used throughout the Specification and are defined below, unless otherwise stated.

"$T_1$": Longitudinal Relaxation Time which is the characteristic time for vertical component of the magnetization vector to reach to equilibrium with its surrounding.

"$T_2$": Transverse Relaxation Time which is the characteristic time for the transverse component of the magnetization vector to decay.

Self-Diffusion Coefficient: referred as "diffusion coefficient". The diffusion coefficient of a constituent when chemical gradient is not present and the movement of molecules is dominated by Brownian motion.

Carr-Purcell-Meiboom-Gill (CPMG) Pulse Sequence: Common NMR pulse sequence for $T_2$ distribution measurement.

"Pulsed Field Gradient": Common pulse sequence for diffusion measurement using the NMR tools that have the capability of applying gradient pulse.

"Diffusion Editing": Common pulse sequence for diffusion measurement using the NMR tools that do not have the capability of applying gradient pulse.

"Emulsion": Mixture of two or more immiscible fluids. There is usually a continuous phase which is the base fluid and a discontinuous phase which is dispersed in the form of fine bubbles/droplets.

"NMR": Nuclear Magnetic Resonance which is the technology which uses magnetic field to measure relaxation rate and diffusion of certain nuclei. Hydrogen nuclei is the nuclei of interest in this invention.

"Surface Relaxivity": measure of how fast a hydrogen nuclei in one fluid phase loses its magnetization as a result of encountering an impermeable boundary.

"WO" or "W/O": water in oil.

"OW" or "O/W": oil in water.

"WC": Water cut also known as the water volume fraction.

The present invention is based on the fact that the relaxation and the diffusion coefficients of oil, gas and water change when they are restricted by boundaries or obstacles. In production fluids or pipelines, foams and emulsions of gas in oil, water in oil and oil in water might occur. In emulsions and foams there are two phases defined: continuous phase and discontinuous phase. The NMR properties of the continuous phase are similar to the NMR properties of the bulk fluid. But in the discontinuous phase, depending on the droplet or bubble size, the NMR properties change significantly. For example the typical $T_2$ time and diffusion coefficient of bulk water are 2.71 s and 2.42×10$^{-9}$ m$^2$/s, respectively. The same properties drop to 1.04 s and 0.045×10$^{-9}$ m$^2$/s, respectively when water forms the discontinuous phase in a 50 vol % WC emulsion. In this invention, 2D diffusion coefficient-transverse relaxation (D-T) measurements are combined with corresponding $T_1$ or $T_2$ measurements for average surface relaxivity calculation at multiple points. Then the surface relaxivity can be used to convert the $T_1$ or $T_2$ measurements to droplet or bubble size.

In order to calculate the droplet size distribution of oil-in-water or water-in-oil emulsions, the method and system generally comprise:

a. Provide a low field NMR relaxometer with the capability of measuring transverse $T_2$, and D-$T_2$;

b. Measure and record $T_2$ and D-$T_2$ for bulk fluids present in the emulsion/mixture;

c. Define the characteristic $T_2$ and D-$T_2$ for each individual fluid constituent of the mixture;

d. Measure and record $T_2$ and D-$T_2$ for at least three emulsion samples;

e. Identify the oil and water peaks for all samples in step d;

f. Convert the diffusion coefficient of the discontinuous phase to droplet size using restricted diffusion model in droplets for all samples in step d;

g. Calculate the surface relaxivity of the emulsion by combining the droplet radius and $T_2$ for each sample in step d and calculate the average surface relaxivity; and h. Measure $T_2$ distribution for various emulsions and convert $T_2$ distributions to droplet size distribution using the surface relaxivity calculate in step g.

In order to calculate the bubble size distribution in gas in oil and gas in water foams the method and system generally comprise:

a. Provide a low field NMR relaxometer with the capability of measuring longitudinal relaxation ($T_1$) and 2D diffusion coefficient-transverse relaxation (D-$T_1$);

b. Measure and record $T_1$ and D-$T_1$ for bulk fluids present in the foam;

c. Define the characteristic $T_1$ and $D$-$T_1$ for each individual fluid constituent of the mixture;
d. Measure and record $T_1$ and $D$-$T_1$ for at least three emulsion samples;
e. Identify the oil or water and gas peaks for all samples in step;
f. Convert the diffusion coefficient of the discontinuous phase to bubble size using restricted diffusion model in bubbles for all samples in step d;
g. Calculate the surface relaxivity of the foam by combining the droplet radius and $T_1$ for each sample in step d and calculate the average surface relaxivity; and
h. Measure $T_1$ distribution for various emulsions and convert $T_1$ distributions to bubble size distribution using the surface relaxivity.

The data received using the present invention can be used to enhance production by controlling pressure to reduce the hydrate formation, or to monitor whether hydrates are forming or have formed during the operation. Furthermore, the information can be used to maintain the pressure above the bubble point of the fluid so that gas does not produce the hydrate formations.

The information can also be used to better manage and execute necessary mitigation method to reduce the hydrate plugging risk. For example, an operator or system can monitor the droplet size distribution since a low droplet size tends to indicate low hydrate plugging risk. However, if the droplet is large (larger than micron size range), there is high tendency for hydrate plugging and operator needs to take necessary action to avoid hydrate plug. Mitigation can include (1) Injection of thermodynamic hydrate inhibitor (TH) to prevent the formation of hydrate slurry; (2) Injection of Anti-agglomerant (AA) to reduce the plugging risk; (3) Injection of Kinetic Hydrate Hydrate Inhibitor (KHI), to delay the formation of hydrate; or 4) Change in the operating condition such as increase temperature (for example by electrical heating), decrease the pressure, etc. The choice of remediation method can depend on the operating condition of the field.

Analysis

The NMR measurements were performed using a 2 MHz Magritek Rock Core Analyzer. All measurements are at room temperature (approximately 25° C.) and pressure (approximately 1 atm). Two main pulse sequences were used to measure the NMR response for emulsion sample: Carr-Purcell-Meiboom-Gill (CPMG) and Pulsed Field Gradient-CPMG Pulse Sequence.

CPMG Pulse Sequence

Figure 2A:
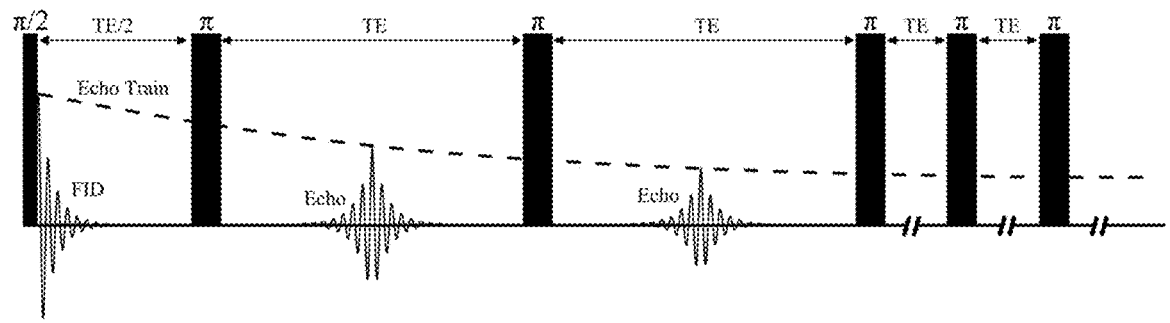
FIG. 2A illustrates a CPMG pulse sequence.

CPMG pulse sequence illustrated in FIG. 2A (modified from Aichele, C. P. et al., *J. Colloid Interface Sci.* 2007, 315 (2), 607. doi:10.1016/j.jcis.2007.07.057) was introduced by Can and Purcell (1954) and then modified by Meiboom and Gill (1958) to measure the transverse relaxation time ($T_2$) of hydrogen nuclei in fluid samples. $T_2$ relaxation mechanism is a combination of three relaxation mechanisms (Equation 1): bulk relaxation ($T_{2B}$), surface relaxation ($T_{2S}$) and diffusion induced relaxation ($T_{2B}$).

$$\frac{1}{T_2} = \frac{1}{T_{2B}} + \frac{1}{T_{2S}} + \frac{1}{T_{2D}} \qquad (1)$$

By minimizing the echo spacing (TE), the diffusion induced relaxation becomes negligible compared to bulk and surface relaxations. Surface relaxation is a function of surface relaxivity and the ratio of surface area to the volume. Assuming spherical bubbles for the discontinuous phase (water in this study), Equation 1 can be rewritten as:

$$\frac{1}{T_2} = \frac{1}{T_{2B}} + \rho \frac{S}{V} = \frac{1}{T_{2B}} + \rho \frac{3}{r} \qquad (2)$$

In which $\rho$ is the surface relaxivity, S is the surface area, V is the volume, r is the droplet radius. This equation can be solved for droplet radius, as reflected in Equation 3:

$$r = 3\rho \left( \frac{1}{T_2} - \frac{1}{T_{2B}} \right)^{-1} \qquad (3)$$

Bulk and $T_2$ distributions in Equation 3 can be measured for the emulsion, the only parameter that is required for DSD calculation is the surface relaxivity. Surface relaxivity determination will be discussed later.

Pulsed Field Gradient-CPMG Pulse Sequence

Figure 2B:
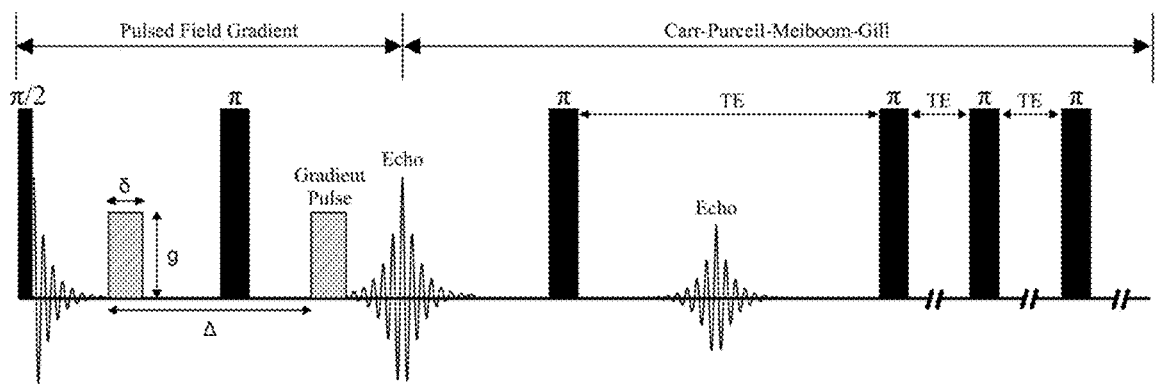
FIG. 2B illustrates a pulsed Field Gradient-CPMG pulse sequence consists of a pulse field gradient (PFG) followed by a CPMG pulse sequence.

Pulsed Field Gradient-CPMG pulse sequence consists of a pulse field gradient (PFG) followed by a CPMG pulse sequence and is illustrated in FIG. 2B. This pulse sequence consists of a pulsed field gradient pulse sequence followed by a CPMG pulse sequence. It is used to measure the D-$T_2$ maps. $\pi$ and $\pi/2$ are the 180 and 90 degrees pulses, $\Delta$ is the diffusion time which is the time between gradient pulses, $\delta$ is the gradient pulse duration, TE is the echo spacing which is the time between two consecutive 180 degrees pulses. This pulse sequence correlates two phenomena: the translational diffusion coefficient of water molecules restricted by droplet walls (replicated in diffusion measurement) and the chemical properties of water and oil (replicated in $T_2$ measurement). A two dimensional distribution function accounts for these phenomena and an inverse Laplace transform is used to produce the D-$T_2$ maps.

Figure 3:
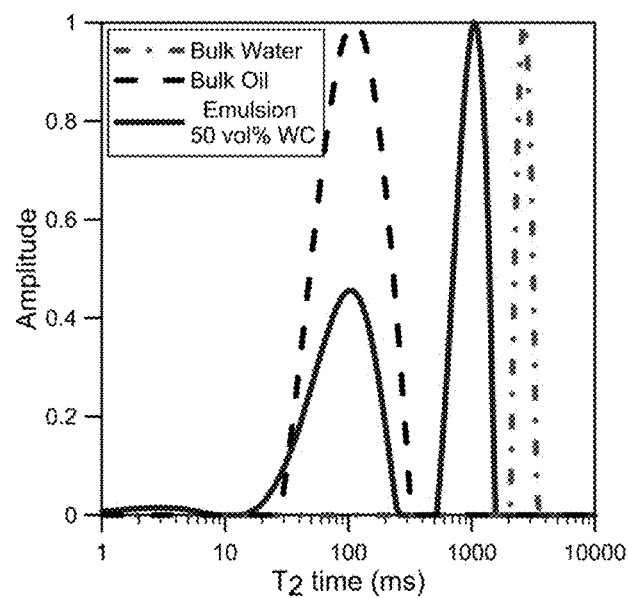
FIG. 3 illustrates the transverse relaxation time ($T_2$) of bulk oil, bulk water and an example of synthetic water in oil emulsion.

FIG. 3 illustrates the transverse relaxation time ($T_2$) of bulk oil, bulk water and an example of synthetic water in oil emulsion. The oil relaxation does not change since oil is the continuous phase but water relaxation changed from 2.71 s to 1.04 s due to restriction of water molecules in the water droplet as the discontinuous phase.

Figure 4A:
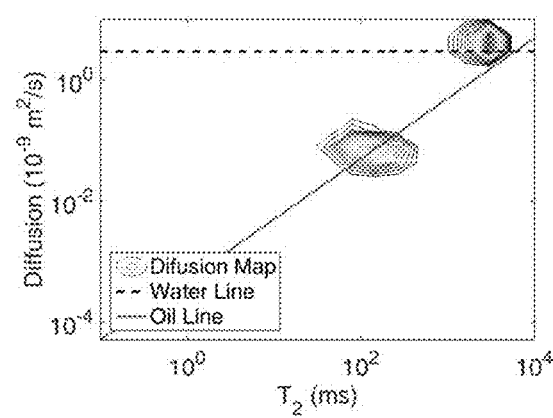
FIG. 4A illustrates the 2D diffusion-relaxation (D-$T_2$) maps from bulk water and oil.
Figure 4B:
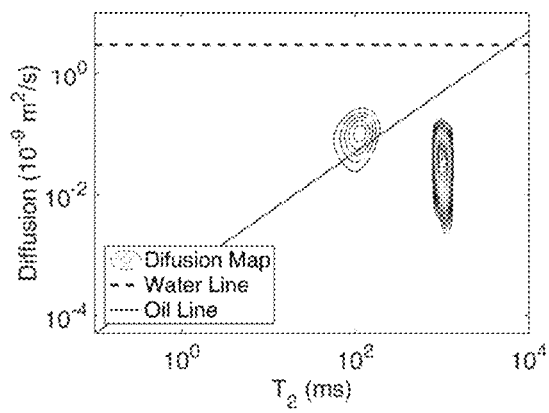
FIG. 4B illustrates the 2D maps for the oil and water (from FIG.; 4A) but in the form of water in oil emulsion (50 vol; % WC)

FIG. 4A illustrates the 2D diffusion-relaxation (D-$T_2$) maps from bulk water and oil and FIG. 4B illustrates the 2D maps for the same oil and water but in the form of water in oil emulsion (50 vol. % WC). The water diffusion decreased significantly due to the restriction of water molecules in water droplets in FIG. 4B, compared to FIG. 4A. The Diffusion coefficient for oil does not change. Increase in relaxation rate and decrease in diffusion coefficient is correlated to the droplet/bubble size in the emulsion/mixture.

Discontinuous phase diffusion coefficient can be measured using only PFG pulse sequence. PFG pulse sequence measures the diffusion coefficient of a combination of both continuous and discontinuous phases. There are two methods to measure the discontinuous diffusion coefficient: In the first approach differentiating the diffusion coefficient requires knowledge of the fraction of the continuous phase which is usually unknown in cases such as oil and gas production wells and pipelines. The second approach is to use very long diffusion times to allow the continuous phase NMR signal to decay during this time period. The disadvantages of this approach are compromising the signal to noise ratio since a major portion of the signal decays due to relaxation before the data acquisition and also applicability only in cases that the continuous phase relaxation is faster than the discontinuous phase.

Figure 5:
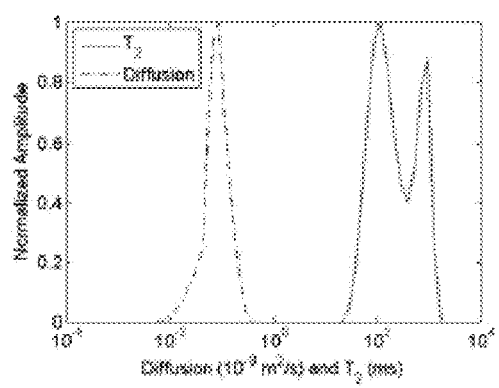
FIG. 5 illustrates the corresponding 1D distributions for time and diffusion.

2D D-$T_2$ maps were used in the present example even though the experiment time is longer than PFG experiments. The 2D maps can differentiate the water and oil not only based on diffusion responses but also based on their respective $T_2$ distributions. FIG. 4B illustrated an example of 2D map for an emulsion sample. The 2D map clearly illustrates two distinct peaks separated both in time and diffusion coefficient dimensions. The corresponding 1D distributions for both time and diffusion are illustrated in FIG. 5. The 1D diffusion does not distinguish water and oil. Differentiation of oil and water in diffusion dimension is the main advantage of the 2D maps. The 2D maps were measured using 30 ms diffusion time, 5 ms gradient pulse duration, 0.5 T/m maximum gradient and 40 gradient steps. The CPMG part of the pulse sequence is ran using the CPMG pulse sequence for 1d $T_2$ experiments.

Droplet Size Calculation

Murday and Cotts (1968) developed a model to relate the echo-signal attenuation to the diffusion coefficient of the fluid and experiment variables is a sphere with specific radius as recited in Equation 4. This equation can be used to calculate the droplet radius using the measured diffusion coefficients. Restricted diffusion in spheres can be analytically modeled using the following set of equations:

$$E(g) = \exp\left(-\frac{2\gamma^2 g^2}{D^2} \times \sum_{n=1}^{\infty} \frac{2\alpha_n^2 D\delta - 2 + 2L(\delta) - L(\Delta - \delta) + 2L(\Delta) - L(\Delta + \delta)}{\alpha_n^6(R^2\alpha_n^2 - 2)}\right) \quad (4)$$

$$L(t) = \exp(-\alpha_n^2 Dt) \quad (5)$$

Where $E(g)$ is the signal attenuation at each gradient step, $\gamma$ is the magnetogyric ratio, g is the gradient amplitude, D is the diffusion coefficient of the fluid, $\delta$ is the gradient pulse length, $\Delta$ is the diffusion time, R is the sphere radius and $\alpha_n$'s are the non-negative solutions of the equation 6 (J is the Bessel function of the first kind).

$$(\alpha_n R)J_{3/2}(\alpha_n R) - \tfrac{1}{2}J_{3/2}(\alpha_n R) = 0 \quad (6)$$

Figure 6:
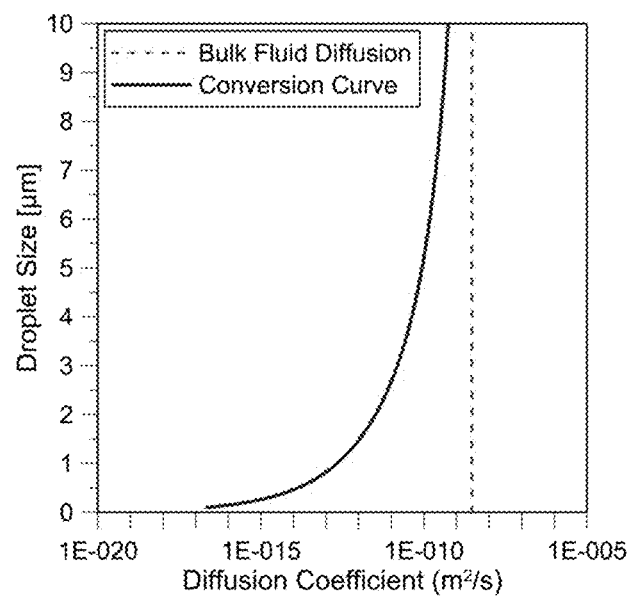
FIG. 6 illustrates a diffusion coefficient curve based on the droplet radius.

Using above sets of equation the droplet radius that results in the experimentally measured diffusion coefficient can be calculated. An example of the conversion curve is illustrated in FIG. 6. This figure is generated using the equations 4 to 6 for specific NMR acquisition parameters such as D, $\Delta$, $\delta$ and g, in this figure where D=2.97E-9, $\Delta$=30 ms, $\delta$=5 ms and g=0.5 T/m.

Surface Relaxivity Calculation

Once the droplet size for one 2D map measurement is calculated, equation 3 can be solved for the surface relaxivity. Since the surface relaxivity is a function of oil and water composition, it is recommended to measure multiple 2D maps and average over all calculated surface relaxivities. Once a universal surface relaxivity for a specific oil and water composition is calculated the $T_2$ distributions can be converted to droplet/bubble size distributions.

EXAMPLES

The application of the current invention was shown in a series of emulsions with various water cuts. The samples were prepared in the laboratory using similar water and oil compositions. The results were tested by comparing the droplet size distributions measured by NMR and microscopy methods.

Emulsion Preparation

Model water-in-oil emulsion consists of a mineral oil, a mixture of surfactants and deionized water. The mineral oil utilized in these experiments was Crystal Plus mineral oil 70T purchased from STE Oil Company Inc. The oil is a Newtonian fluid with viscosity of 20 cP at 25° C. and density of 0.857 g/cm$^3$ at 20° C.

The surfactant mixture consists of a nonionic surfactant, Sorbitan Monooleate (known as Span 80) and an ionic surfactant, Sodium Di-2-Ethylhexylsulfosuccinate (known as AOT). The concentration of surfactant in the model W/O emulsions was 5 wt. % with respect to the total mass of the emulsion. Furthermore, the ratio concentration of the surfactants used in this work was 90 wt. % of Span 80 and 10 wt. % of the AOT. Span 80 was purchased from Sigma Aldirch and used without any further purification. It has a reported molecular weight of 428.61 g/mol and Hydrophilic Lipophilic Balance (HLB) value of 4.3 (Peixinho et al., 2010). AOT surfactant was purchased from Fischer Scientific and has a reported molecular weight of 444.56 g/mol. The water volume fraction (also known as water cut) for this model emulsion system ranges from about 10 to 70 vol. %.

About 30 ml of emulsion was prepared by first dissolving the pre-measured surfactant mixture in the mineral oil at low heat (~50° C.) and medium stirring. Heating was performed using a hotplate and a magnetic stirrer. Next, the sample was cooled to room temperature. Once cooled, it was stirred at 8000 rpm using a high-speed homogenizer while water was dropped slowly using a syringe (Sjöblom et al., 2010). The total stirring time depends on water cut of the emulsion. For emulsions with water cuts≤50 vol. %, the system was stirred for 3 minutes where water was added during the first minute. As for 60 and 70 vol. % water cut emulsions, the system was stirred for 6 minutes and water was added during the first 4 minutes. Longer stirring time was required at high water cut system to allow water to be dropped slowly into the system. This method ensures that W/O emulsion will be produced.

Microscopy Droplet Size Measurement

Water droplet size of the emulsion was measured independently using an optical microscope (Olympus IX71) connected to a digital camera (Olympus XM10). The microscopy images were analyzed using Image J. At each water cut investigated, a minimum of 250 water droplets was measured and the mean droplet size as calculated. The sample was prepared by adding an emulsion drop onto a glass slide and covering with a cover slip to provide a thin layer of droplets on the slide.

NMR Droplet Size Measurements

All the NMR measurements were performed using a 2 MHZ Magritek Rock Core Analyzer at room temperature and pressure. The $T_2$ distributions were measured with 400 µs echo spacing, 50000 number of echoes, constant pulse length of 20 µs for both 90 and 180 degrees pulses and minimum signal to noise ratio (SNR) of 250. The 2D maps were measured using 30 ms diffusion time, 5 ms gradient pulse duration, 0.5 T/m maximum gradient and 40 gradient steps.

Results

Microscopy Droplet Size Measurements

Figure 7A:
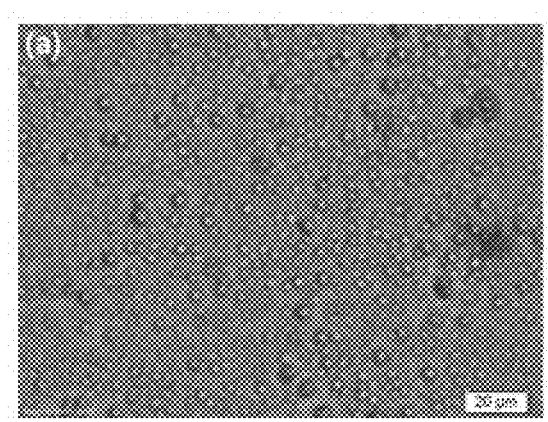
FIG. 7A illustrate the microscopy images of the water-in-oil emulsions prepared using mineral oil 70T at 10 vol; % of water cut.
Figure 7B:
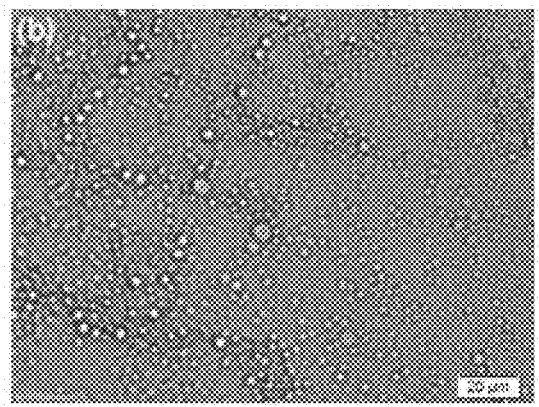
FIG. 7B illustrate the microscopy images of the water-in-oil emulsions prepared using mineral oil 70T at 50 vol; % of water cut.
Figure 8:
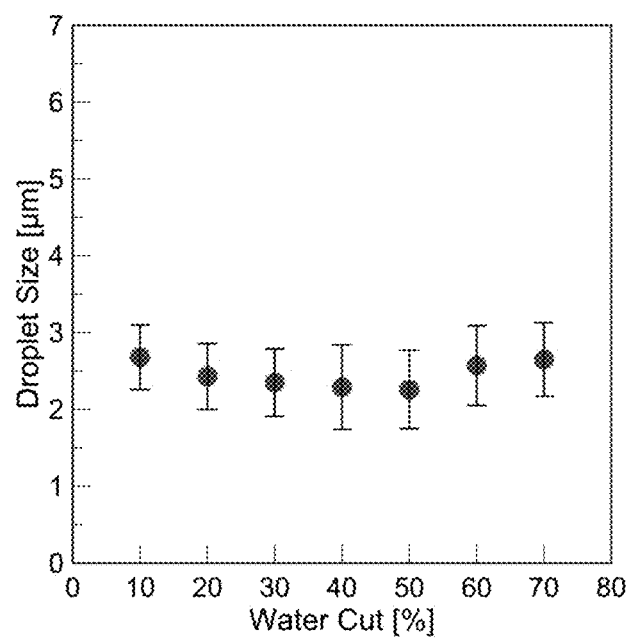
FIG. 8 illustrates a graph of the droplet size as a function of the percent water cut.
Figure 9A:
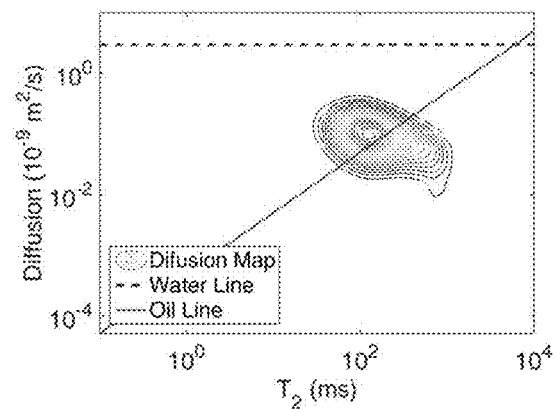
FIG. 9A illustrates a D-$T_2$ map for 10 vol % water cut.
Figure 9B:
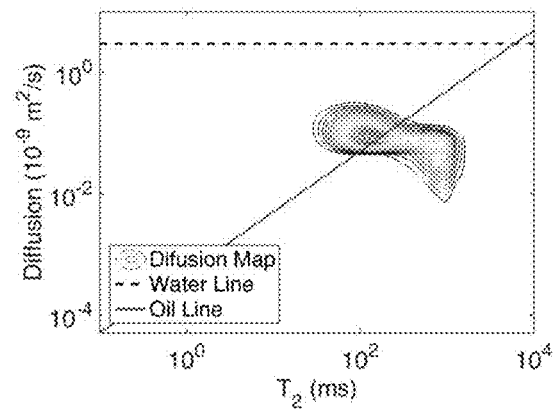
FIG. 9B illustrates a D-$T_2$ map for 20 vol % water cut.
Figure 9C:
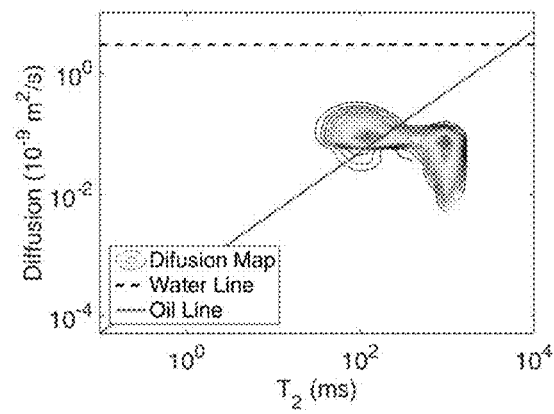
FIG. 9C illustrates a D-$T_2$ map for 30 vol % water cut.
Figure 9D:
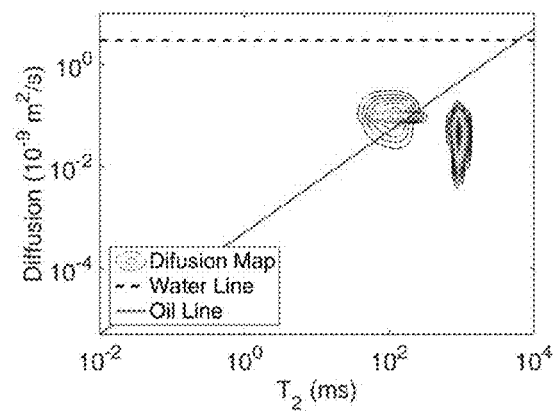
FIG. 9D illustrates a D-$T_2$ map for 40 vol % water cut.
Figure 9E:
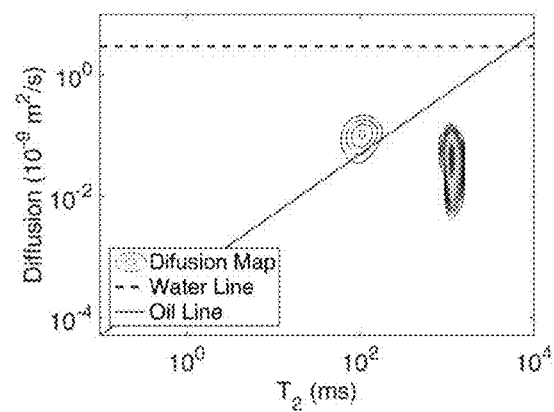
FIG. 9E illustrates a D-$T_2$ map for 60 vol % water cut.
Figure 9F:
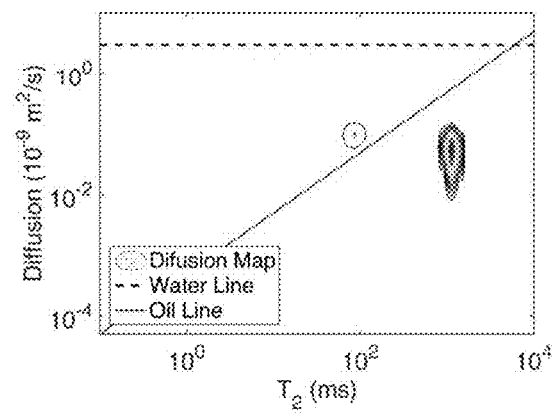
FIG. 9F illustrates a D-$T_2$ map for 70 vol % water cut.

FIGS. 7A and 7B illustrate the microscopy images of the water-in-oil emulsions prepared using mineral oil 70T at 10 and 50 vol. % of water cut, respectively. The optical image shows presence of not one but a distribution of bubble sizes. Analysis of the microscopy images shows that the numerical average droplet size of this emulsion system is in the range of about 2-3 µm across all water cut investigated in this work (FIG. 8). This average droplet size is in agreement with a typical water-in-crude oil emulsion system reported by other researchers (see e.g. Noik et al., *Soc. Petroelum Eng.* 2002. doi: 10.2118/77492-MS).

The microscopy water droplets size measurement illustrated in FIGS. 7A and 7B illustrates that there is minimal change in the size of the water droplets across the water cuts for these experiments. It is believed that the droplet size does not change due to the high concentration of surfactant. The critical concentration of aggregation (CCA), which is the concentration at which inverse micelle form was previously measured to be about 0.1 wt. % for all water cuts. Thus, the emulsions used in these experiments were prepared at concentration above the CCA.

FIG. 8 illustrates microscopy droplet size measurement for mineral oil 70T emulsions at various water cuts. It is to be mentioned here that at each water cut a minimum of 250 water droplets were measured. From these measurements, the average droplet size and its standard deviation was calculated. The error bar in FIG. 8 represents the standard deviation in the measurements. This average droplet size is in agreement with a typical water-in-crude oil emulsion system reported by other researchers.

NMR Droplet Size Measurements

FIGS. 9A-F illustrate a D-$T_2$ map for (FIG. 9A) 10 vol % WC, (FIG. 9B) 20 vol % WC, (FIG. 9C) 30 vol % WC, (FIG. 9D) 40 vol % WC, (FIG. 9E) 60 vol % WC, (FIG. 9F) 70 vol % WC. A 50 vol % WC was illustrated in FIG. 4B. The change in oil signal amplitude and water diffusion coefficient and $T_2$ relaxation as a result of change in water content are observed clearly in FIG. 9. The oil signal amplitude decreases as the water cut increases but neither the $T_2$ time nor the diffusion coefficient for oil phase changes. The water amplitude increases as the water cut increases. Both $T_2$ and diffusion coefficients change as a result of varying water content.

Figure 10A:
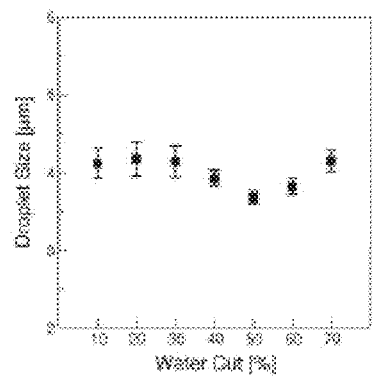
FIG. 10A illustrates NMR droplet size measurements for mineral oil 70T across all water cut emulsions measured by converting diffusion coefficients to droplet size.

FIG. 10A illustrates NMR droplet size measurements for mineral oil 70T across all water cut emulsions measured by converting diffusion coefficients to droplet size. The droplet sizes are measured by converting the diffusion coefficient of the water phase to droplet size. Note that the bars denote distribution of sizes around the mean/principle size represented by the solid symbols. As can be seen in FIG. 10A, the average droplet size is ~4 Similarly, the size of water droplets shows minimal change with change in the water cut of the system. The relatively constant water droplet size across the water cut is believed to be due to the high concentration of surfactant used in this study. However, it is to be mentioned here that the minimum water droplet size observed at 50 vol. % water cut is relatively small and thus insignificant.

Figure 10B:
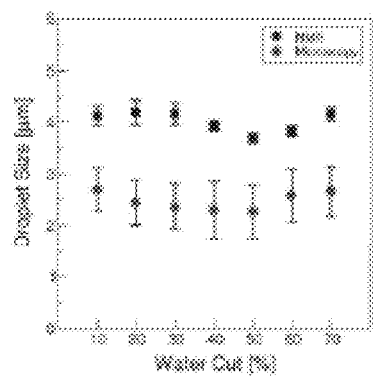
FIG. 10B illustrates droplet size for NMR and microscopy as a function of water cut percentage.

Furthermore, it can be seen in FIG. 10B that in both methods, the trend of the water droplets across all water cuts studied is relatively similar; both show a minimum droplet size at 50 vol. % water cut. This illustrates that the NMR method of the present invention is able to measure the water droplet size in emulsion systems. In addition, it should be noted that when comparing the two methods, larger deviation was observed for the microscopy method results as compared to the NMR method. It is thought that this large deviation in the size of the water droplet measured is due to the optical microscopy method that was used. In optical microscopy, actual position of the droplets in the z-axis (vertically) could not be determined. Consequently, the droplets that are far from the lens appear smaller in the pictures taken. The size of the droplets was measured regardless of the vertical position of the droplets size and the result was taken into the calculation of the average droplet size. This resulted to a smaller average droplet size.

Figure 11:
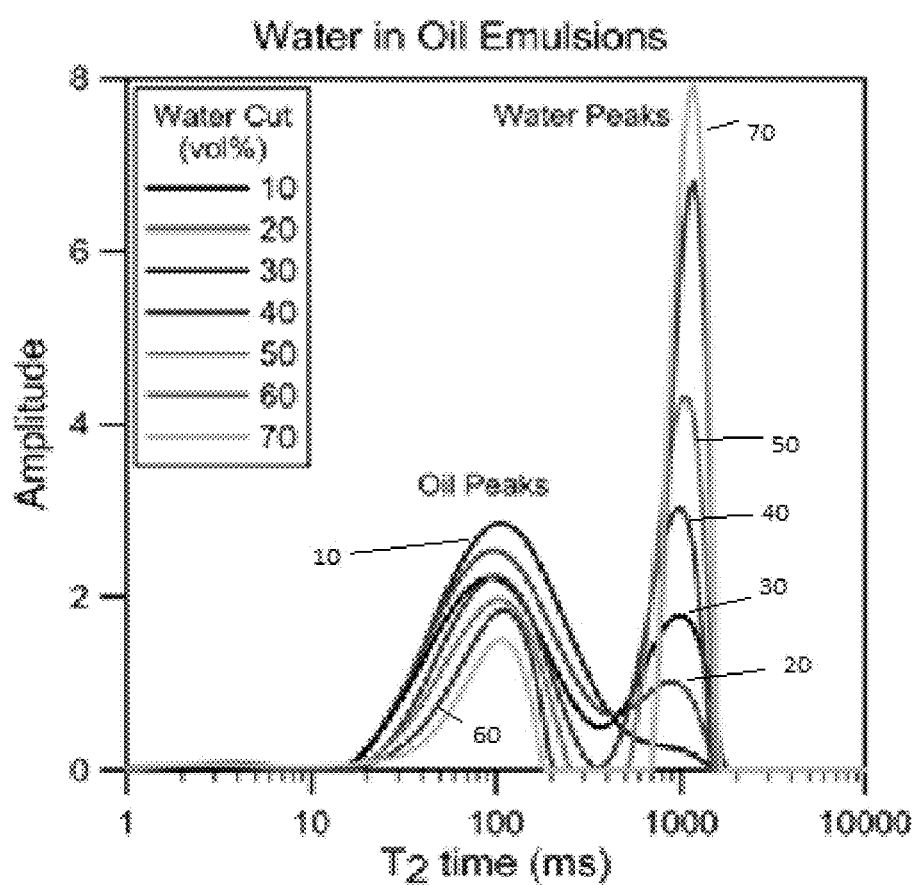
FIG. 11 illustrates the $T_2$ distributions for emulsions measured using the CPMG pulse sequence (FIG. 1)
Figure 12:
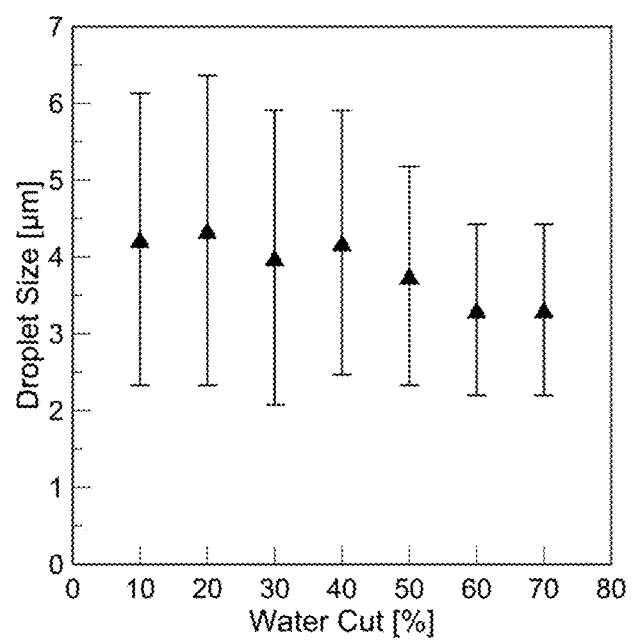
FIG. 12 illustrates the droplet size distribution calculated by converting the $T_2$ distribution of the water phase using the average surface relaxivity.

FIG. 3 illustrated the $T_2$ distribution for bulk oil and water. FIG. 11 illustrates the $T_2$ distributions for emulsions measured using the CPMG pulse sequence (FIG. 1). Bulk responses show a clear distinction between oil and water $T_2$ distributions (FIG. 3). When oil and water are emulsified, the discontinuous phase (water) $T_2$ response is affected by the emulsion properties. The $T_2$ relaxation times for oil do not change by varying the water cut because oil is the continuous phase. $T_2$ response for water varies depending on the water cut. The surface relaxivity for the emulsions can be calculated by solving Equation 3 for p. The $T_2$ distribution of the water phase was used for samples with water cut of 50-70 vol % since they show a distinct peak for water phase. The average surface relaxivity is 0.801 µm/s. The calculated average surface relaxivity was about 1.22 µm/s. Using this surface relaxivity, the droplet size derived from $T_2$ distributions varies from 3.3 to 4.7 µm which is close to the range of the droplet size measured by diffusion method (FIG. 12). By having this surface relaxavity value, droplet size of any T2 distribution for this mineral oil and water system can be calculated using Equation 3.

FIG. 12 illustrates the droplet size distribution calculated by converting the $T_2$ distribution of the water phase using the average surface relaxivity. Note that the bars denote distribution of sizes around the mean/principle size represented by the solid symbols.

Ranges have been discussed and used within the forgoing description. One skilled in the art would understand that any sub-range within the stated range would be suitable, as would any number within the broad range, without deviating from the invention.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed:

1. A method of determining a droplet size distribution of an emulsion, wherein the emulsion is one of an oil-in-water emulsion or a water-in-oil emulsion comprising:
    providing a low field nuclear magnetic resonance (NMR) relaxometer wherein the low field NMR relaxometer is capable of measuring at least one of a transverse relaxation ($T_2$), and a two-dimensional diffusion coefficient-transverse relaxation (D-$T_2$);
    measuring at least one of $T_2$ and D-$T_2$ for produced fluids in the emulsion;
    identifying at least one oil peak and at least one water peak from a Carr-Purcell-Meiboom Gill (CPMG) pulse sequence for the emulsion;
    converting the D-$T_2$ of the discontinuous phase to bubble size using a restricted diffusion model in bubbles;

calculating the surface relaxivity of a foam by combining a droplet radius and longitudinal relaxation ($T_1$) for the produced fluids in the emulsion;

measure the $T_1$ for the emulsion; and determining the droplet size distribution in the emulsion.

2. The method of claim 1, further comprising determining a downhole formation pressure with the droplet size distribution.

3. The method of claim 1, wherein at least four $T_2$ and $D-T_2$ measurements are performed.

4. The method of claim 1, wherein the droplet size distribution is measured over time.

5. The method of claim 1, further comprising determining the existence or lack of existence of a hydraulic plug caused by the emulsion.

6. The method of claim 5, wherein a mitigation treatment is performed if there is the existence of the hydraulic plug caused by the emulsion.

7. The method of claim 6, wherein the mitigation is at least one of an injection of thermodynamic hydrate inhibitor, injection of an anti-agglomerant, injection of kinetic hydrate inhibitor (KHI) or change at least one operating condition.

8. The method of claim 7, wherein the at least one operating condition is temperature or a pressure.

9. A method of assessing gas hydrate slurry formation and a hydrate plugging risk by determining the droplet size distribution of oil-in-water or water-in-oil emulsions, comprising:

providing a low field nuclear magnetic resonance (NMR) relaxometer to a emulsion, wherein the low field NMR relaxometer is capable of measuring transverse relaxation ($T_2$), and 2D diffusion coefficient-transverse relaxation ($D-T_2$);

measuring the $T_2$ and the $D-T_2$ for bulk fluids present in a gas hydrate slurry;

defining a characteristic of the $T_2$ and the $D-T_2$ for each individual fluid constituent of the slurry;

measuring the $T_2$ and the $D-T_2$ for at least three samples of the slurry;

identifying oil peaks and water peaks for the at least three samples of the slurry;

converting the diffusion coefficient of a discontinuous phase of the slurry to droplet size using a restricted diffusion model in droplets for the at least three samples;

calculating surface relaxivity of the slurry by combining a radius of the droplet and the $T_2$ for the at least three samples;

measuring a $T_2$ distribution for the at least three samples of the slurry;

converting the $T_2$ distribution to a droplet size distribution with the surface relaxivity; and comparing the droplet size distribution information with a database of droplet size distribution date to assess the relative risk of hydrate formation.

10. The method of claim 9, wherein at least four $T_2$ and $D-T_2$ measurements are performed.

11. The method of claim 9, wherein a mitigation treatment is performed if there is a higher probability of the hydraulic plug forming caused by the emulsion.

12. The method of claim 11, wherein the mitigation is at least one of an injection of thermodynamic hydrate inhibitor, injection of an anti-agglomerant, injection of a kinetic hydrate inhibitor or changing at least one operating condition, wherein the at least one operating condition is temperature or pressure.

* * * * *